United States Patent [19]

Casanova et al.

[11] Patent Number: 5,244,546
[45] Date of Patent: Sep. 14, 1993

[54] PROCESS FOR PREPARING TETRAALKYL BUTANETETRACARBOXYLATES

[75] Inventors: Eduardo A. Casanova, Ballwin; John H. Wagenknecht, Cedar Hill, both of Mo.

[73] Assignee: Monsanto Company, St. Louis, Mo.

[21] Appl. No.: 450,773

[22] Filed: Dec. 14, 1989

[51] Int. Cl.$^5$ ................................................. C25C 1/00
[52] U.S. Cl. ................................................. 204/59 R
[58] Field of Search ................................................. 204/59 R

[56] References Cited

U.S. PATENT DOCUMENTS

| | | | |
|---|---|---|---|
| 3,274,084 | 9/1966 | Baizer | 204/72 |
| 3,390,066 | 6/1968 | Baizer | 204/72 |
| 4,076,601 | 2/1978 | White | 204/59 R |
| 4,659,441 | 4/1987 | Noding | 204/59 R |

OTHER PUBLICATIONS

Baizer et al "Organic Electrochemistry An Introduction and A Guide" 2nd ed. Marcel Dekker New York 1983 p. 200.
Chemical Abstract 90: 5921u 1979 p. 5926.
Chemical Abstract 96: 34508u 1982 p. 602.
Chemical Abstract 74–75980f Giovanni et al p. 407 (1971).

*Primary Examiner*—John Niebling
*Attorney, Agent, or Firm*—W. W. Brooks

[57] ABSTRACT

The present invention is directed to a process for preparing tetraalkyl butanetetracarboxylates by electrolytic hydrodimerization of dialkyl maleates in alkanols.

13 Claims, 2 Drawing Sheets

PROCESS FOR PREPARING TETRAALKYL BUTANETETRACARBOXYLATES

BACKGROUND OF THE INVENTION

1. Field of the Invention

The present invention is directed to a process for preparing tetraalkyl butanetetracarboxylates by electrolytic hydrodimerization of dialkyl maleates in alkanols.

The compound 1,2,3,4-butanetetracarboxylic acid has been found by the U.S. Department of Agriculture to be an effective permanent press agent for polycotton fabrics, and the compound could find use in large quantities for such purpose. Accordingly, an efficient process for preparing the compound could be very useful. Such a process must produce a product of acceptable color performance properties, as this is an important factor for suitability for permanent press agents. The electrolytic process of the present application produces the tetraalkyl 1,2,3,4-butanetetracarboxylates, and such compounds can be converted to 1,2,3,4-butanetetracarboxylic acid, as described and claimed in our commonly assigned copending application Ser. No. 07/450,760 Case 43-21(7833).

2. Description of the Related Art

Electrolytic reductive couplings of various activated olefins have been investigated and reported in the past. Much of this work involved aqueous systems in a divided cell, and often with a supporting electrolyte salt with a very negative discharge potential, such as a quaternary ammonium salt. In addition to reductive couplings, other reactions such as simple reduction and polymerization frequently occur. Various parameters of such reactions have been discussed, including use of various electrolytes, see Organic Electrochemistry, edited by Manuel M. Baizer and Henning Lund (1983, Marcel Dekker, N.Y., N.Y.). At page 669 of this reference, it is stated that undivided cells are operable with the restrictions that (1) the olefin and product not be substantially oxidized at the anode, and (2) the oxygen evolved at the anode in aqueous systems not promote undesirable side reactions. This reference also refers, for example at pages 669 and 672, to dimerization of diethyl maleate and the effect of alkali metal cations in increasing the rate of dimerization of anion radicals.

Electrolytic hyrodimerization of diethyl maleate has been reported by Baizer and Petrovich, *J. Electrochem. Soc.*, 114 (10), 1024–1025 (1967); the described procedures utilized a catholyte of water and dimethylformamide in a divided cell and indicated, all other conditions being the same, more hydrodimerization occurs in the presence of tetraethylammonium ion than of sodium ion. The electrolyses were carried out for three (3) hours, generally resulting in about 50% conversions, and specified amounts of hydrodimer, and other products.

Methanol has been used as a solvent for study of reduction mechanisms. See Dimitra Sazou et al, "Electrochemical Reduction of Maleic and Fumaric Acids and Their Dimethyl Esters in Methanol at a Mercury Electrode", Dimitra Sazou et al, *Coll. Czech. Chem. Comm.*, 52, 2132–2141 (1957). Cyclic voltammograms of the acids in methanol solution with various supporting electrolytes, employing a hanging mercury drop electrode, are given, and reduction mechanisms discussed. The double bond reduction of the corresponding dimethyl esters was stated to take place in one step. The described procedures utilized very dilute solutions of the acids, e.g. 0.0025 or 0.005 moles per liter.

SUMMARY OF THE INVENTION

The present invention concerns a useful preparative process for tetraalkyl butanetetracarboxylates which involves effecting electrolytic hydrodimerization of substantial concentrations of dialkyl maleate in a medium comprising alkanol, with marked advantage in the selectivities and yields obtained, and conditions which can be employed. The invention further involves effecting such hydrodimerization in an undivided cell employing a metal salt, particularly an alkali metal salt, as supporting electrolyte. The alkanol, employed in substantially dry form, can serve as a proton donor to effect addition of hydrogen ion during the reaction. The use of alkanol, rather than water as the electrolysis medium, substantially avoids hydrolysis of the maleate ester groups, and the acidification of the medium which would result from such hydrolysis. It has been found, surprisingly, that in an alkanol medium, with an undivided cell, good yields of tetraalkyl butanetetracarboxylate can be obtained, and that the yields in electrolyses employing sodium or other alkali metal salts can even exceed those in electrolyses employing tetraalkylammonium salts. The presence of alkanol essentially prevents hydrolysis of the dialkyl maleate, even in the presence of basic salts, as solvolysis of an alkyl group replaces it with an alkyl group. Therefore alkyl acid maleate is not formed in significant quantity, and the medium does not become strongly acidic. The hydrodimerization can therefore be carried to high conversion with good yields of hydrodimer, rather than with increasing amounts of reduction product, dialkyl succinate, resulting from acidification of the medium, as is characteristic of electrolytic hydrodimerizations of dialkyl maleate in aqueous media. In aqueous media there is a shift from alkaline to acidic conditions during the electrolysis, and the pH usually declines to about 4. In the absence of water in an alkanol medium, such acidic pH conditions do not develop and a marked increase in succinate product is not observed. The present process is marked by an absence of substantial amounts of monoalkyl maleate in the electrolysis medium. It is very advantageous that the present process can be conducted efficiently in an undivided cell, thereby avoiding the additional electrical resistance, membrane expense, and other adverse factors involved in operating with a divided cell. The invention generally involves use of electrolysis solutions with very substantial concentrations of maleate reactant and use of fairly substantial electrical current in the electrolysis, and obtaining substantial amounts of tetraalkyl butanetetracarboxylate product in reasonable reaction time.

DESCRIPTION OF THE PREFERRED EMBODIMENTS

Figure 1:
FIG. 1 is a drawing with bar graphs illustrating yields of tetramethyl butanetetracarboxylate and other products obtained by electrolysis in methanol with various electrolytes.

The present process can be conducted with dialkyl maleates in general, but for practical considerations, only the maleates with lower alkyl groups, e.g. of 1 to 6 carbon atoms, are likely to be of much interest. Dimethyl maleate is the preferred reactant, and is used in exemplifications herein, but diethyl maleate, dipropyl maleate, dihexyl maleate, etc. can be used. Electrical resistance tends to increase with increasing alkyl size, whether in the ester or in the alkanol solvent, thereby making electrical power usage less efficient. It is also disadvantageous to employ alkanols of such high molecular weight that they tend to be solids at ambient temperature.

As discussed herein, an important use for tetraalkyl butanetetracarboxylates involves conversion to butanetetracarboxylic acid. The simplest ester, the tetramethyl ester, serves very well for this purpose and there will ordinarily be no reason to choose other tetraalkyl esters as intermediates for the same product.

The reactions presumably occurring in the present process can be pictured:

cathode:

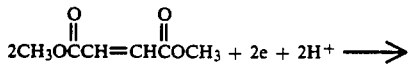

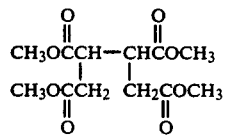

anode:

$$2CH_3OH - 2e \longrightarrow 2H^+ + CH_3OCH_2OH$$

Sum:

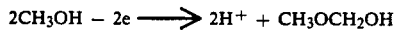

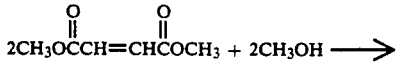

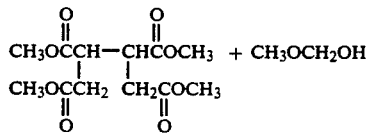

Methoxymethanol, the hemiacetal of formaldehyde, is also a likely product. The presence of formaldehyde has been confirmed, but it may be formed by disassociation of methoxymethanol. Additional possible intermediates include $+CH_2OH$ and $\bullet CH_2OH$ in the anode reaction, and acetic acid from protons and acetate electrolyte (if used). Also, alkoxides, e.g. $CH_3O^-$, can be produced as a result of reaction at the cathode.

With $\bullet CH_2OH$ as a likely intermediate at the anode, it presents the possibility of adding at the maleate double bond to cause production of other by-products, thereby possibly causing considerable loss in selectivity to the desired hydrodimer when an undivided cell is used; however, this undesirable side reaction does not appear to occur to any extent as good results are obtained in an undivided cell. It may be that the use of an undivided cell is actually advantageous, as it permits protons generated at the anode to move very freely to protonate methoxide produced in conjunction with the hydrodimerization at the cathode, thereby avoiding possible interfering reactions of the methoxide and polymerization.

It has fortunately been found that the present process can not only be carried out very efficiently with simple alkali metal salts as supporting electrolyte, but that the results with such salts are actually better than those obtained with some of the more expensive electrolytes which are commonly used. In addition to the preferred alkali metal salts, the present process can use other supporting electrolytes known to the art.

The electrolysis uses supporting electrolytes to provide ions to carry the current in the process. In general, any electrolytes can be employed which dissociate into ions in the electrolysis medium to carry current, and which do not unduly interfere with the desired reactions or cause excessive losses to competing reactions. Most of the electrolytes can be considered salts, as having a cation from a base and an anion from an acid. However, it is also feasible to employ bases as the electrolytes, and this may at times be appropriate in order to counter acidity. The dialkyl maleates are subject to reduction at less negative potentials than many suitable cations, so competitive discharge of cations is not ordinarily a concern. Alkali metal compounds such as sodium, potassium or lithium compounds, can be employed, as well as alkaline earth metal compounds, and quaternary ammonium compounds, which are characterized by very negative discharge potentials. Acid anions will in general be operative as the anionic portion of the electrolyte, but will generally be selected to have acceptable solubility in the alkanol system, and to minimize interfering or competing reactions and electrode degradation. Among operable anions are carboxylic acid anions, halide ions, and aromatic sulfonic acid anions.

In the present invention it has fortunately been found that a very simple salt, e.g. sodium acetate, serves very well as an electrolyte in the electrohydrodimerization of alkyl maleates. In the prior art quaternary ammonium salts have usually been considered to give better results in electrohydrodimerization than do alkali metal salts. However, in the present invention alkali metal salts have been found capable of giving better results in the electrohydrodimerization of dimethyl maleate, particularly with respect to selectivity to desired product. Among the useful electrolytes are sodium, potassium and lithium acetates, propionates, and succinates, sodium toluenesulfonates, tetrabutylammonium p-toluenesulfonate, tetrabutylammonium hydroxide, tetrabutylammonium acetate, tetrabutylammonium chloride. Similar salts can be used with sulfate, phosphate and tetrafluoroborate anions, but such salts tend to cause anode degradation when preferred graphite anodes are used. Some halide salts, e.g. sodium halide, have very limited solubility in methanol, and are therefore inconvenient for use. With regard to calcium chloride, the chloride is theorized to be relatively tightly bound to the calcium and to act as an acid catalyst to cause formation of dialkyl 2-methoxysuccinate (conveniently referred to herein as methoxydialkylsuccinate), making selectivity very poor to the desired hydrodimer. Calcium acetate has poor solubility, but calcium nitrate is better in this regard.

The present electrolysis process can be carried out over a broad range of electrolytic conditions, including a wide range of strengths of applied electric currents and current densities at the electrodes. The process is operable at very low current densities, such as less than 5 milliamperes per square centimeter to more than 100 or 200 milliamperes per square centimeter. Preferred current densities are apt to be in the range of about 15 to about 50 or so milliamperes per square centimeter, with operation, for example at 25 milliamperes per square centimeter giving good product selectivity at relatively low cell voltage, with good electrode life. There is advantage in having high current density in order to maximize cell utilization, but this is to be balanced against the high cell voltage and resistance and heat generation which add to costs.

The present electrolysis can be operated over a broad range of concentrations, such as from less than about 5% to more than about 50% by weight of the dialkyl maleate reactant, and good selectivities to the desired dimer products are obtainable over broad ranges. Concentrations from at least 15% to 35% to 40% or so are usually very suitable, and product concentrations in the same range are also very suitable, although they will be lower in specific cases because of less than 100% yields and conversions. The process is suitable for large scale production, making kilograms or more quantities of product. The use of relatively high concentrations of reactant lessens the amount of materials to be handled. However, the electrical resistance of the solution rises with the concentration of reactant. In addition, solubility considerations may be a factor at some higher concentrations. It is desirable, although not necessary, to operate with all components in a homogeneous phase during the electrolysis.

The concentration of supporting electrolyte can vary widely, but it is unnecessary to have more than very dilute concentrations for conductivity. Higher concentrations will improve conductivity, but salts in general are not very soluble in methanol, and there is ordinarily no advantage in using amounts of salts in excess of their solubility. The amount of salt can be just a minimum amount to give electrical conductivity, but will generally be in a range of 0.5 to 2 or 3% or so by weight, and for practical purposes, seldom over 5% or so by weight. In order to minimize expense, the salt concentrations will be kept low, as the cost of replenishing or recycling the salts will increase with the amount of the salt. The preferred operation will employ a relatively inexpensive salt, e.g. sodium acetate, which can be disposed of, rather than recycled.

The concentration ranges of maleate reactant set forth herein are, in general, initial concentrations, as the concentration will change during the electrolysis process, which will generally be run as a batch reaction, or a series of batch reactions. The electrolysis reaction will ordinarily be run to fairly high conversion, reacting more than 75% or 80% of the maleate, because selectivity to desired product is still good at high conversions, and in order to avoid unnecessary steps, handling and expense in separating unreacted maleate from the dimer product for recycle. It will be preferred to operate at maleate conversions approximately 95% or so. Higher conversions are possible, but it has been found that significant electrode degradation occurs if the electrolysis is continued with little or no maleate reactant present.

It has been found that there is a competing chemical side reaction which produces dimethyl 2-methoxysuccinate (conveniently referred to herein as methoxydimethylsuccinate). The amount of this reaction is generally dependent upon the time of exposure of the maleate reactant to the components of the reaction system. Therefore it may be desirable to operate the electrolysis as a series of batch reactions, with relatively low initial maleate concentration and addition of more maleate in subsequent batches of the series. The last batch could then be taken to high conversion prior to product separation. Another approach to minimizing maleate contact time is to use an electrolysis cell which is large, particularly with respect to electrode surface area, compared to the amount of material in the reaction system and maleate reactant. Another approach is a constant stirred tank reactor with a continuous feed and discharge where the DMM concentration is maintained low to diminish the chemical driving force for this side reaction.

The control of reaction time can also be expressed in terms of electrical current supply. The conversion of a particular amount of maleate reactant requires a corresponding number of ampere hours of current, and the time to accumulate a requisite number of ampere-hours in an electrolysis can be varied by changing the current, or the number, or size of the electrolysis cells. A reaction in accord with descriptions herein within 15 hours is fairly efficient, but a reaction time of no more than 10 hours will give less by-product. If the same current is involved, a 16-cell aggregate as described herein will accumulate ampere-hours at twice the rate of an 8-cell aggregate. Of course, the 16 cells also use higher voltage for equivalent current. Cells for large scale production are contemplated as using at least 5 amperes, and more likely 10 or more amperes. Taking into consideration the amperage and number of cells employed, the present process will ordinarily use current and maleate amounts such that no more than 100 grams of dimethyl maleate are present per cell-ampere, and preferably less than 50 grams, or possibly even less than 25 grams dimethyl maleate per cell-ampere. (The term cell-ampere is number of cells $\times$ amperes, and is equivalent to ampere-hours per hour).

The present electrolysis can be effected with the usual electrodes employed in electrohydrodimerization and other reductive coupling reactions. Various metal and graphite electrodes are suitable. The preferred electrodes will generally have relatively high hydrogen overvoltages, such as greater than that of copper. However, lower overvoltage electrodes can be used. Among the cathode materials which can be used are graphite, graphite felt, mercury, copper amalgam, gold, copper, cadmium, tin and aluminum, with graphite, graphite felt, and lead being among the better materials. Mercury is an effective cathode, but its liquid state makes it unsuitable for common flow cell configuration. Graphite electrodes, whether plate or felt, have been found to give the best results. It is an advantage of the present process, and surprising, that it can be conducted with superior results at graphite electrodes. Graphite is much less expensive than many other electrode materials, such as platinum or even lead or cadmium electrodes. It does not add heavy metals to the solution via corrosion, and is suitable for anodes as well as cathodes.

The present electrolysis can be carried out well with an alkanol, e.g. methanol, as the only material employed as carrier for the maleate ester and electrolyte salt. Ordinary industrial grades of methanol, which are substantially water-free, are very suitable for use. Traces of water picked up from contact with the atmosphere will not ordinarily be sufficient to affect results. For example, 2000 ppm water in solution has negligible effect.

However, the presence of more than traces of water will preferably be avoided, as even a small percentage of water can cause a decline in selectivity, and the presence of more than, say 5% by weight, of water is very undesirable. If desired, co-solvents can be used along with the alkanol, particularly such aprotic solvents as dimethylformamide and dimethyl sulfoxide or acetonitrile. Use of co-solvents will not generally be desirable, but there may be particular cases where solubility or other factors would make co-solvents worthwhile.

At the end of the electrolysis reaction the tetraalkyl butanetetracarboxylate product is present in solution in the electrolysis medium, for example, at a concentration of about 25% by weight. The tetraalkyl butanetetracarboxylate product can be separated by crystallization from the solution, followed by filtration. In the case of tetramethyl butanetetracarboxylate (TMBTC), the crystallization is effected by cooling, e.g. to below 0° C., usually between 0° C. and −10° C. The separation removes the product from the electrolysis medium and also separates it from residual maleate reactant and succinate and alkoxysuccinate by-products. The butanetetracarboxylate tetraester product can then be subjected to hydrolysis and purification procedures to prepare butanetetracarboxylic acid suitable for permanent press use, as described in the above-identified copending applications.

The invention is illustrated by the following examples.

EXAMPLE 1

An electrolysis was carried out in a jacketed resin pot, using water as an electrolysis medium, with dimethyl maleate present as a second phase, constituting 22% by weight of the electrolysis medium. The cathode was lead, and the anode was platinum. A mixture of tetrabutylammonium nitrate and tetrabutyl ammonium hydroxide was employed as electrolyte, and electrolysis was conducted at a current density of 30 milliamperes per square centimeter of cathode surface. The electrolysis began at a basic pH, but rapidly became more acidic due to base catalyzed hydrolysis of dimethyl maleate, leading to monomethyl maleate. The pH quickly approached a value of 4. Analysis showed a weight ratio of 47 parts tetramethyl butanetetracarboxylate to 22 parts of dimethyl succinate, a simple reduction product of the starting maleate. This amounts to a selectivity of only 2.1 parts hydrodimer to 1 part of the succinate material. It is apparent that the acidic conditions are causing a large loss to a simple reduction reaction, and that even the use of a basic electrolyte did not prevent the development of acidic conditions. The analysis of the electrolysis medium also showed unreacted dimethyl maleate, with it being present in a ratio of 41 parts to the 47 and 22 parts of hydrodimer and succinate products. Thus the reaction had been taken to only a relatively low conversion. Similar results were obtained in other runs with aqueous media, employing the undivided resin pot cell and graphite or lead cathodes with platinum anodes, at current densities varying from 30 to 70 milliamperes per square centimeter. Electrolytes utilized included tetrabutylammonium nitrate, tetraethylammonium p-toluenesulfonate, tetrabutylammonium hydroxide and tetrabutyl ammonium sulfate. The ratio of hydrodimer to succinate varied from the 2.1 reported above, to 0.43, with higher values being obtained when excess tetrabutylammonium hydroxide was present in an attempt maintain a high pH.

EXAMPLE 2

Electrolyses were carried out utilizing an undivided resin pot cell as described in Example 1, but using methanol as the medium. Results for a number of electrolyses, with quaternary ammonium electrolytes with some variation in conditions and electrodes, are set forth in Table 1. In the Table, the numerical values for dimethyl maleate (DMM), dimethyl succinate (DMS), and tetramethyl butanetetracarboxylate (kTMBTC) are reported in terms of analytical values, which can be compared to give the ratios of the reported materials. The ratio of TMBTC to DMS ranged from as high as 2.55 in Run 1, down to 0.89 in Run 3, with the results in general being better than those with water as solvent. The Runs 5 and 6 used, respectively, 90% methanol and 33% methanol, with the results being inferior to those obtainable with undiluted methanol.

TABLE 1

| Run | Elec | Cath | Anode | Pl (%) | Temp (°C.) | CD (mA/cm$^2$) | DMM | DMS | MeODMS | TMBTC |
|---|---|---|---|---|---|---|---|---|---|---|
| 1 | TBAFB | Gr | Pt | 26 | 25 | 70 | 68 | 29 | | 74 |
| 2 | TBAFB | Hg | Pt | 26 | 25 | 40 | 5 | 18 | 35 | 45 |
| 3 | TBAFB | Gr | Pt | 26 | 25 | 70 | 9 | 45 | | 40 |
| 4 | TBAH | Gr | Gr | 26 | 25 | 70 | 0 | 39 | | 42 |
| 5x | TBAFB | Gr | Pt | 25 | 25 | 70 | 20 | 30 | | 55 |
| 6xx | TEAT | Pb | Pt | 15 | 25 | 30 | 31 | 35 | | 41 | x 90% methanol in water
xx 33% methanol in water

In Table 1 and elsewhere in the specification abbreviations will at times be used as designations as follows:
DMM is dimethyl maleate;
DMS is dimethyl succinate;
MeODMS is methoxydimethyl succinate;
TMBTC is tetramethylbutane tetracarboxylate;
TBAFB is tetrabutylammonium tetrafluoroborate;
TBAH is tetrabutylammonium hydroxide;
TEAT is tetraethylammonium-p-toluenesulfonate;
Pl is the payload in % by weight DMM in solution; and
CD is current density in milliamperes/cm$^2$.

EXAMPLE 3

The undivided resin pot cell of Example 1 was utilized with methanol as the medium and small concentrations of metal salts as electrolyte, with results reported in Table 2.

TABLE 2

| Run | Elec | Cath | Anode | Pl (%) | Temp (°C.) | CD mA/cm$^2$ | DMM | DMS | MeODMS | TMBTC |
|---|---|---|---|---|---|---|---|---|---|---|
| 1 | NaOAc | Felt | Gr | 25 | 15 | 50 | 0 | 12 | 2 | 86 |

TABLE 2-continued

| Run | Elec | Cath | Anode | Pl (%) | Temp (°C.) | CD mA/cm² | DMM | DMS | MeODMS | TMBTC |
|---|---|---|---|---|---|---|---|---|---|---|
| 2 | Na₂Suc | Gr | Gr | 25 | 15 | 50 | 0 | 22 | 32 | 55 |
| 3 | KOAc | Gr | Gr | 26 | 27 | 70 | 1.7 | 8.2 | 1.8 | 15.6 |
| 4 | LiOAc | Gr | Gr | 26 | 28 | 70 | 2.5 | 4.5 | 1.5 | 16.2 |

It is demonstrated that good selectivities can be obtained by employing alkali metal salts in methanol, as seen from the 7.17 hydrodimer to succinate ratio (86/12) in Run 1, with sodium acetate. High conversions, also were obtained as shown by the low or zero values for dimethyl maleate in the product solution.

EXAMPLE 4

Electrolyses were conducted in a small flow cell of parallel plate design with a gap between electrodes of about 1 mm, and cathodes of 19 cm². Flow through the cell was at about 1 liter/minute. The cell was connected to a jacketed reservoir which was cooled by tap water (at about 15° C.). Electrolyses were conducted with dimethyl maleate, and about 1% by weight of a selected metal salt, in methanol, with results as reported in Table 3.

TABLE 3

| Run | Elec | Cath | Anode | Pl (%) | Temp (°C.) | CD (mA/cm²) | DMM | DMS | MeODMS | TMBTC |
|---|---|---|---|---|---|---|---|---|---|---|
| 1 | NaOAc | Gr | Gr | 44 | 25 | 50 | 15 | 20 | 6 | 71 |
| 2 | LiOAc | Gr | Gr | 42 | 27 | 50 | 47 | 13 | 7 | 37 |
| 3 | LiOAc | Gr | Gr | 26 | 27 | 50 | 9 | 34 | 3 | 59 |

While there was considerable variation in these and other results in the cell, ratios of dimer to succinate as high as 3.5 were obtainable employing alkali metal salts in methanol.

EXAMPLE 5

Electrolyses of dimethyl maleate were carried out in methanol employing various electrolytes. The electrolysis cell was a jacketed resin pot of 150 ml capacity, fitted with a magnetic stirring bar, graphite plate electrodes (5 cm by 5 cm by 0.5 cm) with 25 cm² of cathode surface facing the anode. The cell was cooled with tap water (15° to 20° C.) Power was supplied by a constant current power supply, generally set at 1 ampere. The cell was charged with 75 g methanol, 25 g dimethyl maleate, and 1 to 2 g of supporting electrolyte. Electrolysis was started and continued until nearly all of the dimethyl maleate was consumed as determined by gas chromatography. Selectivity to the three major products (as a percentage of the three products) was determined by gas chromatography, and shown in the bar graphs of FIG. 1. It will be noted that high TMBTC selectivities are obtained with the alkali metal acetates, particularly with lithium and sodium acetates. The illustrated results are based on generally comparable procedures. While other results may be obtained under other conditions, the illustrated results show that high selectivities are obtainable, and this is consistent with the selectivities consistently obtainable, particularly with sodium acetate, under standard conditions in other procedures. Halide anions were operable, although at a very low selectivity with CaCl₂. The high levels of methoxydimethylsuccinate indicate that use of CaCl₂ and LiCl results in catalytic methoxylation, a competing reaction.

EXAMPLE 6

Figure 2:
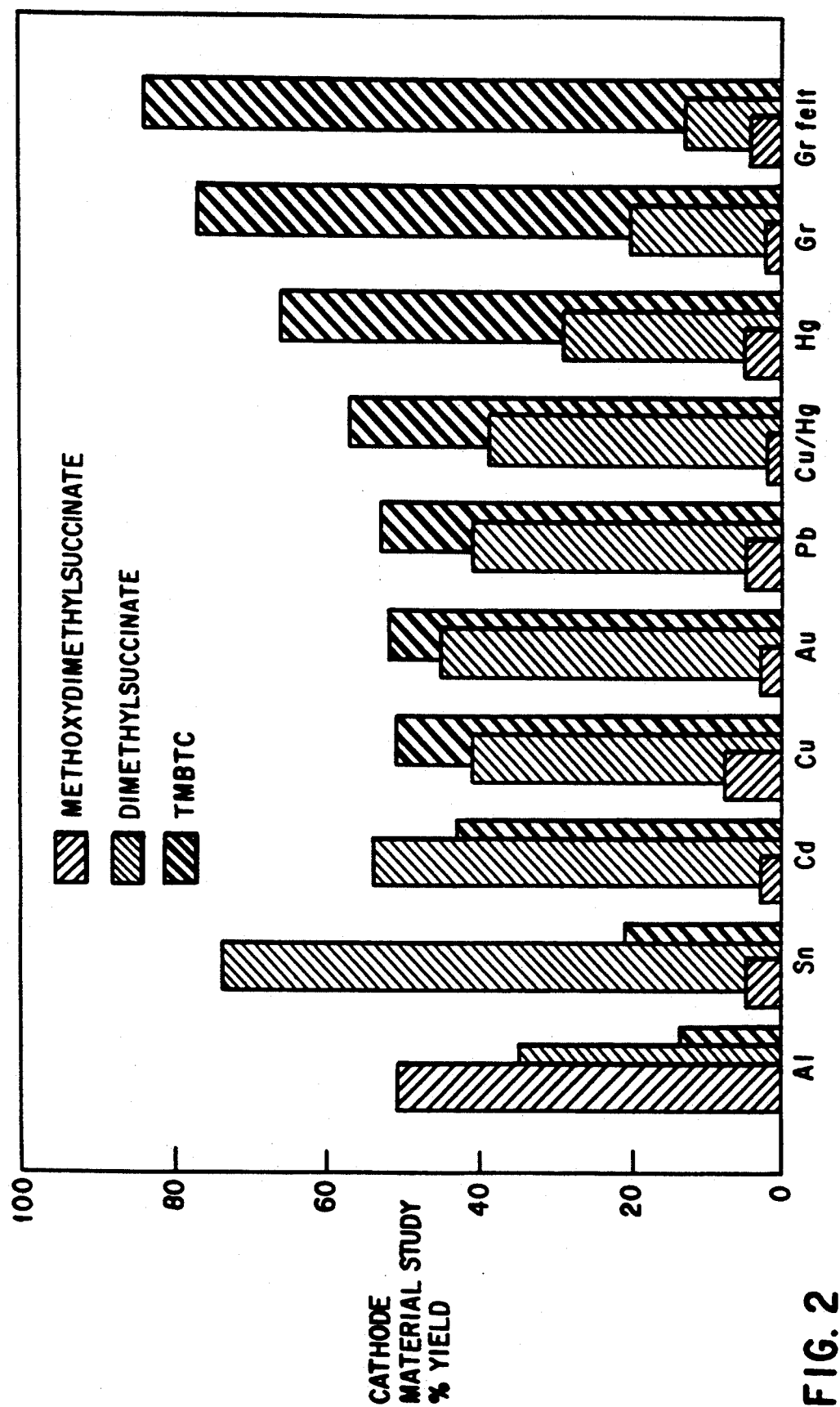
FIG. 2 is a drawing with bar graphs illustrating yields of tetramethyl butanetetracarboxylate and other products obtained by electrolysis in methanol employing various cathodes.

Electrolysis was conducted as in Example 5, with sodium acetate as electrolyte, and employing various cathodes. The selectivities obtained for the three major products are illustrated in the bar graphs of FIG. 2.

EXAMPLE 7

A large flow cell was utilized to prepare tetramethyl butanetetracarboxylate in an electrolysis with sodium acetate as electrolyte. The cell was a modified Electro Syn Cell, (Svenska Utveklingsaketbologet, Swedish National Development Company) with 8 cells, later modified to 16 cells. The cell has 500 cm² graphite plates with about 1 mm spacing and plastic screens between electrodes to aid in flow dispersion. The cell was attached by poly(vinyl chloride) piping to a centrifugal pump, 18.93 liter (5 gallon) reservoir and stainless steel heat exchanger. The system was charged with about 8 kg dimethyl maleate, 15 kg of methanol and 200 g sodium acetate. The solution was circulated through the cell at about 75.7 liters (20.0 gallons) per minute. The cell was operated at 12.5 amperes (65-90 volts) for about 7.5 hours (with 16 cells). Typical analysis of the resulting solution was 25% tetramethyl butanetetracarboxylate, 5% dimethyl succinate, 5% methoxydimethylsuccinate, 5% dimethyl maleate, and the balance methanol.

To describe in more detail, the cell had been modified to operate in a bipolar mode with only the end plates attached to the electrical supply. Stated quantities (reported in Table 4 below) of dimethyl maleate, methanol and sodium acetate were charged into the reservoirs as listed under DMM, MeOH and NaOAc. The circulation pump was activated and circulation was effected to achieve sample homogeneity, at a flow rate of 75.7 liters—79.5 liters (20-21 gallons) per minute. A sample was drawn at time zero, with DMM usually below charge quantity because of dilution by residue of a previous run. The power supply was activated and electrolysis conducted at 25 MA/cm² until the power was shut off at reported times. A sample was drawn and analytical results reported as %'s of reaction mixture, along with the selectivities to the products determined therefrom, and the grams of DMM which had reacted. Results of three different runs are reported in Table 4. Product selectivity as high as 83% was obtained in the third run, and thus, like the other runs in methanol, was carried to a high conversion, the conversion of dimethyl maleate being over 95%, based on the maleate in the product sample analysis, and the amount of reacted maleate. A comparison of Run 1 with an 8 cell electrolysis, to Runs 2 and 3 with 16 cell electrolysis, shows that increasing the cells can cut the reaction time and also cut the amount of methoxydimethylsuccinate product, thereby improving selectivity to the desired hydrodimer. In general the production of the by-product, produced by a chemical reaction, can be lessened by operating with a high electrolysis cell through-put compared to reservoir capacity, or other means to cut reaction time, as well as by limiting payload or lowering reaction temperature.

TABLE 4

| Run | Temp °C. | DMM g | MeOH g | NaOAc g | Time hr | PROD. MIX. ANAL., % | | | | |
|---|---|---|---|---|---|---|---|---|---|---|
| | | | | | | DMM | MeOH | DMS | MeODMS | TMBTC |
| 1 (8 cells) | 23.0 | 9515 | 12950 | 200 | 0.0 | 37.0 | 59.3 | 0.6 | 2.7 | 2.2 |
| | | | | | 14.1 | 1.9 | 54.9 | 4.8 | 11.4 | 25.8 |
| 2 (16 cells) | 21.3 | 8230 | 13000 | 200 | 0.0 | 38.6 | 62.3 | 0.2 | 1.1 | 0.7 |
| | | | | | 7.3 | 2.2 | 61.3 | 5.4 | 5.3 | 28.8 |
| 3 (16 cells) | 20.1 | 8020 | 14810 | 200 | 0.0 | 33.5 | 66.3 | 0.7 | 1.0 | 2.7 |
| | | | | | 7.3 | 1.4 | ? | 3.5 | 4.0 | 21.7 |

| Run | SELECTIVITIES, % | | | CONVERSIONS % |
|---|---|---|---|---|
| | TMBTC | DMS | MeODMS | DMM |
| 1 (8 cells) | 73.1% | 10.2% | 16.7% | 96.1 |
| 2 (16 cells) | 77.6% | 13.7% | 8.7% | 95.1 |
| 3 (16 cells) | 83.1% | 9.0% | 8.0% | 95.9 |

What is claimed is:

1. A process for producing a tetraalkyl 1,2,3,4-butanetetracarboxylate which comprises subjecting a liquid electrolysis medium comprising a substantial concentration of a dialkyl maleate, an alkanol corresponding to the alkyl groups of the dialkyl maleate, and an alkanol-soluble alkali metal carboxylate supporting electrolyte to electrolysis in an electrolysis cell, using a graphite anode and a graphite cathode, to effect a reductive coupling of the dialkyl maleate to yield the tetralkyl 1,2,3,4-butanetetracarboxylate.

2. The process of claim 1 in which the alkanol-soluble alkali metal carboxylate supporting electrolyte is sodium acetate.

3. The process of claim 1 in which the dialkyl maleate is dimethyl maleate, the alkanol is methanol, and the tetraalkyl 1,2,3,4-butanetetracarboxylate is tetramethyl 1,2,3,4-butanetetracarboxylate.

4. The process of claim 1 in which the electrolysis is carried to a high conversion with very little saponification of the dialkyl maleate reactant.

5. The process of claim 1 in which the electrolysis is conducted at a rate sufficient to keep the amount of dialkyl 2-methoxysuccinate produced in a competing chemical reaction to a value less than 5% of the dialkyl maleate reacted.

6. The process of claim 1 in which the electrolysis is conducted in an undivided cell.

7. The process of claim 1 in which sodium acetate is employed as electrolyte.

8. The process of claim 3 in which the tetramethyl 1,2,3,4-butanetetracarboxylate is separated from the electrolysis medium by cooling and crystallation.

9. The process of claim 3 in which the initial concentration of dimethyl maleate is at least 15% by weight and the electrolysis is continued until at least about 95% of the dimethyl maleate has reacted.

10. The process of claim 9 in which a flow cell with graphite electrodes is used at current densities of at least 15 mA/cm$^2$.

11. The process of claim 10 in which the current densities are in the range of 15 to 100 mA/cm$^2$.

12. The process of claim 1 in which kilogram quantities of the tetraalkyl 1,2,3,4-butanetetracarboxylate are produced in no more than 10 hours.

13. The process of claim 1 in which the liquid electrolysis medium comprises no more than trace amounts of water.

* * * * *

UNITED STATES PATENT AND TRADEMARK OFFICE
CERTIFICATE OF CORRECTION

PATENT NO. : 5,244,546
DATED : September 14, 1993
INVENTOR(S) : E. A. Casanova et al It is certified that error appears in the above—identified patent and that said Letters Patent is hereby corrected as shown below:

In column 8, line 16, after the word "attempt" insert --to-- therefor.

In column 8, line 26, delete "(kTMBTC)" and insert --(TMBTC)-- therefor.

Signed and Sealed this

Twenty-seventh Day of September, 1994

Attest:

BRUCE LEHMAN

Attesting Officer

Commissioner of Patents and Trademarks